(12) United States Patent
Sandifer

(10) Patent No.: US 6,251,087 B1
(45) Date of Patent: Jun. 26, 2001

(54) CASTING PLATE SIZE MEASURING DEVICE FOR AN ORTHOSIS

(75) Inventor: Alan T. Sandifer, Winter Springs, FL (US)

(73) Assignee: Orthomerica Products, Inc., Newport Beach, CA (US)

( * ) Notice: Subject to any disclaimer, the term of this patent is extended or adjusted under 35 U.S.C. 154(b) by 0 days.

(21) Appl. No.: 09/420,921

(22) Filed: Oct. 19, 1999

(51) Int. Cl.[7] .......................................... A61B 5/00
(52) U.S. Cl. .............................................. 600/592
(58) Field of Search ................................ 600/587, 592; 33/3 A, 3 B, 3 C, 511, 512

(56) References Cited

U.S. PATENT DOCUMENTS

| | | |
|---|---|---|
| 2,078,368 | 4/1937 | Brannock . |
| 2,200,223 | 5/1940 | Brown . |
| 2,394,149 | 2/1946 | Clarke . |
| 2,593,385 | 4/1952 | Digate . |
| 3,854,212 | 12/1974 | Rose . |
| 4,993,429 | 2/1991 | Krinsky ................................ 128/779 |
| 5,678,566 | 10/1997 | Dribbon ................................ 128/779 |
| 5,800,364 | 9/1998 | Glennie et al. ........................ 600/592 |

*Primary Examiner*—Max Hindenburg
(74) *Attorney, Agent, or Firm*—Price and Gess

(57) ABSTRACT

The present invention sets forth a foot measuring device that assists the practitioner in selecting the correct size casting plate for fitting a patient with an orthosis. It is designed to measure the distance between the patient's heel and the sulcus of his toes. By providing a more accurate measurement of a patient's foot through the heel to sulcus measurement, the fitting of a casting plate is more precise. An accurate fit provides proper biomechanical alignment, better positioning of the foot, and even pressure distribution of weight over the foot. Even pressure distribution promotes improved balance, stability, support and enhanced sensory feedback.

34 Claims, 4 Drawing Sheets

US 6,251,087 B1

CASTING PLATE SIZE MEASURING DEVICE FOR AN ORTHOSIS

BACKGROUND OF THE INVENTION

1. Field of the Invention

This invention relates to improvements in a foot measuring device, more specifically, a casting plate size measuring device for an orthosis that aids a practitioner in selecting the correct size casting plate for properly fitting a patient's orthosis.

2. Description of Related Art

Various types of devices have been proposed in the past, which would permit a foot to be measured. For example, the Brannock patent, U.S. Pat. No. 2,078,368, describes a foot measuring instrument for fitting shoes by which both feet can be measured at the same time in order to insure an accurate measurement of slightly different size feet. During operation, the foot measuring instrument's slide member, design to indicate the width of the foot, is shifted by a ball joint abutment through a suitable motion transmitting structure when the ball joint abutment is being adjusted to the ball joint of the foot. The slide member, indicating the width of the shoe in correlation with the length as indicated by the ball joint abutment, is brought against the side of the foot. The width indication, taken from the graduations opposite the numerals on the slide member, correspond to the reading of the ball joint abutment along its slide. In relation, the widthwise reading is taken from a line on the slide member that opposes the edge of the foot when the slide member is set in accordance with reading of the ball joint abutment.

The Brown patent, U.S. Pat. No. 2,200,223, is designed to facilitate the operation of fitting a person's feet for shoes by accurately measuring the width and length of the person's feet, coordinating the width and length measurements and avoiding computation and possible errors through the use of reference charts.

The Clarke patent, U.S. Pat. No. 2,394,149, discloses a foot measuring device that accurately determines the length size measurement from heel to toe and from heel to ball measurements. Subsequently, the width size measurement is automatically adjusted to compensate for variations in the length size measurement by evenly applying uniform pressure to all points of contact with the foot. Based upon the length and width size measurements read by the operator, the proper shoe size may be determined. The Clarke patent provides a measuring stick with an affixed heel plate and a movable toe plate in relation to the stick. The toe plate has a parallel bar linkage for mounting a laterally movable side plate whereby the width of the foot is determined by the movement of the side plate with respect to the toe plate.

The Digate patent, U.S. Pat. No. 2,593,385, shows a foot measuring device that indicates both the length and width of an individual's foot. During the measurement process, the heel and sole of the foot contact fixed surfaces on the device. The measurements are then taken without requiring the removal of the individual's foot from the device. The measurement is conducted by implementing one movable or adjustable element.

The Rose patent, U.S. Pat. No. 3,854,212, describes a foot measuring device consisting of a molded plastic bench with a molded plastic slide mounted on the bench. The bench has marking indicia, added to the formed surface, to indicate an accurate dimension and a converter to translate the dimensions into the appropriate shoe sizes.

Numerous devices have been proposed in the past that would permit a foot to be fitted for an orthosis. More specifically, the Krinsky patent, U.S. Pat. No. 4,993,429, shows an orthotic fitting system and method. An envelope and an adjacent diverticulum are connect to one another and are filled with a known amount of viscous fluid. The diverticulum has indicia on it capable of indicating what portion of the fluid is within the diverticulum. The envelope is fitted against a portion of a patient's body, which is to be cushioned, and the fluid adjusts between the envelope and the diverticulum to provide proper cushioning for the foot. Flow communication is stopped between the diverticulum and the envelope and the amount of fluid in the diverticulum is determined from the indicia. An orthotic device in the shape of the envelope is then formulated containing the amount of fluid, which remained in the envelope of the fitting device.

The Glennie et al. patent, U.S. Pat. No. 5,800,364, provides an apparatus and method for recording characteristics of a person's foot and for interpreting the results to design a functional foot orthosis. As the person undergoes a movement routine, video cameras view the person's foot in real time from below, from the front, from the right side and from the rear to produce simultaneous images which together give a three dimensional record of a person's foot. During analysis, selected video images from the recordings are calibrated and analyzed geometrically to ascertain the characteristics of the person's foot. A functional orthosis is then designed and manufactured by a computer-aided apparatus.

Whatever the precise merits, features and advantages of the above cited references, none of them achieves or fulfills the purpose of the present invention. The orthosis field is constantly seeking a closer, more accurate fit of a patient's foot to his orthosis.

SUMMARY OF THE INVENTION

The present invention sets forth a foot measuring device that assists the practitioner in selecting a correct size casting plate for fitting a patient with an orthosis. It is designed to measure the distance between the patient's heel and the sulcus of his toes. By providing a more accurate measurement of a patient's foot through the heel to sulcus measurement, the fitting of a casting plate is more precise. An accurate fit provides proper biomechanical alignment, better positioning of the foot, and even pressure distribution over the foot. Even pressure distribution promotes improved balance, stability, support and enhanced sensory feedback.

A casting plate size measuring device includes an elongated member, a fixed member fastened to the elongated member and an indicia member shaped to accommodate the underside of the toe and slidably mounted to the elongated member.

BRIEF DESCRIPTION OF THE DRAWINGS

The exact nature of this invention as well as other objects and advantages thereof will be readily apparent from consideration of the following detailed description in conjunction with the accompanying drawings in which like reference numerals designate like parts throughout the figures and wherein.

DETAILED DESCRIPTION OF THE PREFERRED EMBODIMENTS

The following description is provided to enable any person skilled in the art to make and use the invention and sets forth the best modes, contemplated by the inventor, for carrying out his invention. Various modifications, however, will remain readily apparent to those skilled in the art, since the generic principles of the present invention have been defined herein specifically to provide a readily and easily manufacturable casting plate size measuring device for measuring a patient's foot for an orthosis.

Figure 1:
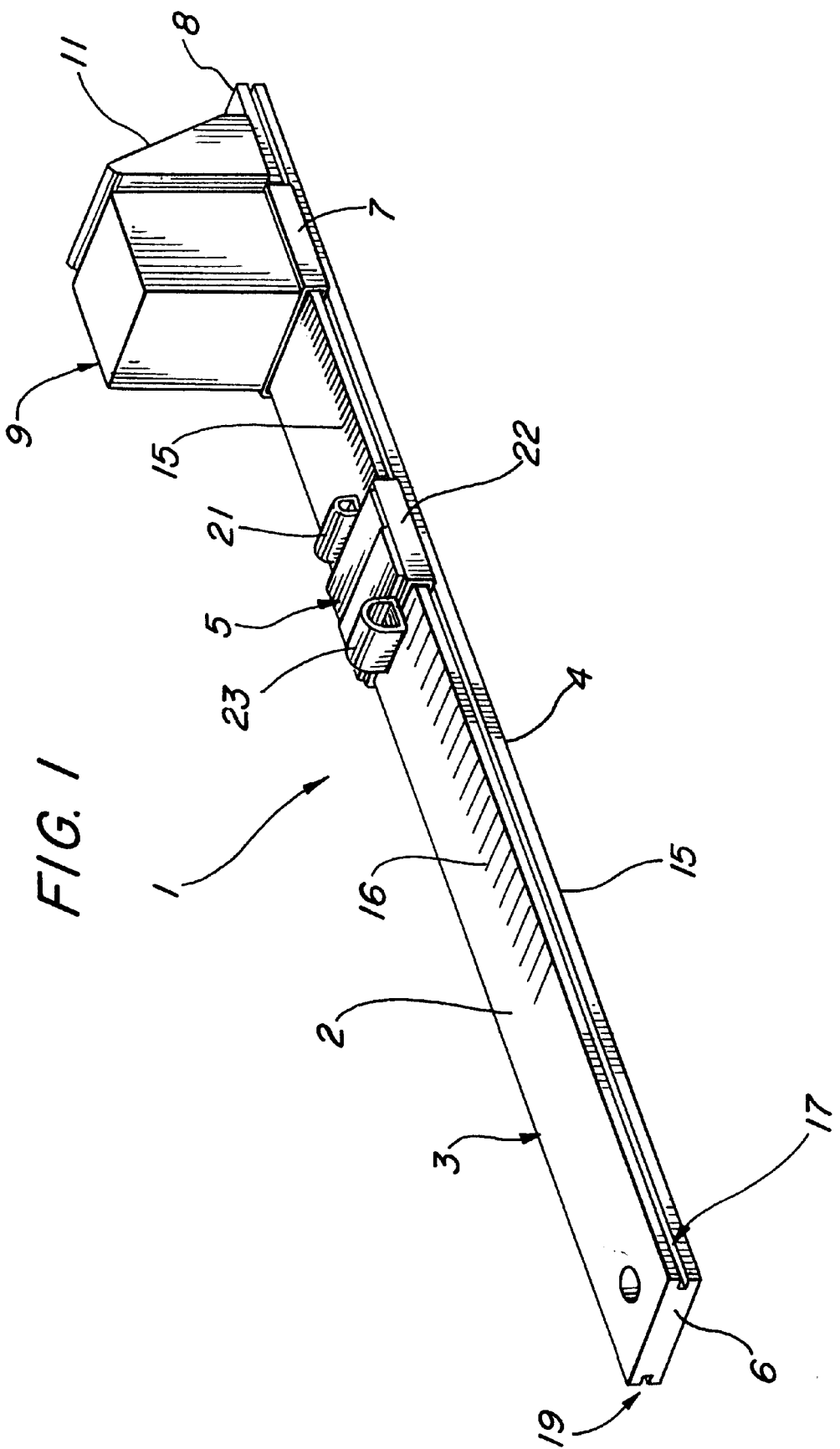
FIG. 1 is a perspective view showing the preferred embodiment of the casting plate size measuring device.

FIG. 1 is a perspective view showing a preferred embodiment of a casting plate size measuring device 1 for an orthosis. The casting plate size measuring device 1 includes an elongated support member 3, a fixed member 11, a movable block member 9 and a measurement slider or indicia member 5. It is contemplated that the elongated support member 3 may be constructed of any metal, alloy, wood, plastic, a plastic composite or any other suitable material and may range from twelve to twenty-four inches in length and 0.25 to 4 inches in width. In the preferred embodiment, the elongated support member 3 includes a set of first and second sides 2, 4 and a set of first and second shorter sides 6, 8.

A scale 16 may be printed, etched, silk-screened or otherwise placed on either side 2 or 4. The scale 16 may be added by any convenient means, such as, by making the marks on a carrier and placing the carrier and the markings on the elongated support member 3, as by means of delcomania. The delcacomania process may be used in conjunction with glass, metal or plastic materials. If, for example, the elongated support member 3 was constructed of plastic, an economical method of producing a molded plastic member 3 with markings is first to mold the elongated support member 3, allow the elongated support member 3 to cool to room temperature, and then apply the markings to the surface of the elongated support member 3 to create the scale 16. The scale 16 is marked in order to indicate the length of the patient's foot. As illustrated, the scale 16 is disposed adjacent to the side 6 of the elongated support member 3. It is further contemplated that the scale 16 may be alternatively located adjacent to the side 8 of the elongated support member 3. A scale 15, printed, etched, silk-screened or otherwise placed on either side 2 or 4, is marked in order to indicate the width of the patient's foot when the movable block member 9 abuts the fixed member 11. As illustrated, the scale 15 is disposed adjacent to the side 8 of the elongated support member 3. It is contemplated that the scale 15 may be alternatively located adjacent to the side 6 of the elongated support member 3 and the delcacomania process may be used to apply the markings to the elongated support member 3. In the preferred embodiment, both scale 15 and 16 implement the U.S. Customary and British Imperial System whereby an inch equals to one twelfth of a foot or 2.54 centimeters. Both scale 15 and 16 may also implement the metric system.

The fixed member 11, having a face 13, is designed to facilitate the length and width measurements and is mounted on either side 2 or 4 of the elongated support member 3. The fixed member 11, located at a distal end of the elongated support member 3 and constructed of any metal, alloy, wood, plastic, plastic composite or other suitable material, ranges from 1.5 to 2.5 inches in length, 1.0 to 2.0 inches in width and 1.25 to 1.50 inches in height.

The movable block member 9 ranges from 1.25 to 1.75 inches in length, 1.25 to 1.75 inches in width and 1.25 to 1.75 inches in height. The movable block member 9 is slidably mounted on either side 2 or 4 of the elongated support member 3 due to the association of the attached sliding member 7 and grooves 17 and 19. The movable block member 9 may attach to the sliding member 7 by staples, screws, nails, tacks or other suitable attachment means. Both sides of the sliding member 7 have an inwardly turned flange at its lower margin that rides in the respective grooves 17 and 19 of the elongated support member 3. It is contemplated that a coiled spring or the like may urge the upper portion of the sliding member 7 outwardly away from the movable block member 9 to anchor its flanges in the grooves 17 and 19 of the elongated support member 3 and thus hold the movable block member 9 in a position of adjustment. In order to move the movable block member 9 along the elongated support member 3, the operator may press in the upper portion of the sliding member 7 against the action of a spring with his thumb, and thus release the engagement of the flanges permitting a movement of the movable block member 9 longitudinally of the elongated support member 3 to a new position of adjustment.

Instead of implementing the grooves 17 and 19 for sliding and adjustment, the sliding member 7 may capture or encompass the set of first and second sides 2, 4 and the set of first and second shorter sides 6, 8. By capturing all of the sides of the elongated support member 3, the sliding member 7 will provide durability and resistance to typical wear and tear. A pair of ribs may be incorporated into the sliding member 7 to fix the movable block member 9 in a desired position during the measurement process. The movable block member 9 may also be slidably mounted on the side 2 of the elongated support member 3 through guide slots.

Figure 6:
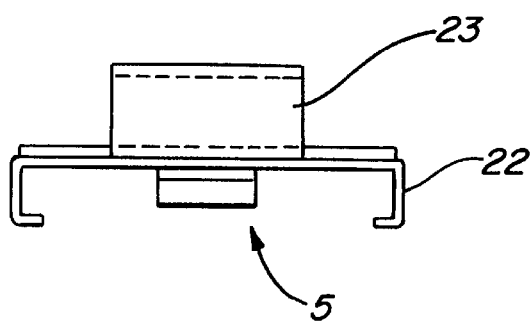
FIG. 6 is front plan view of the measurement slider.
Figure 7:
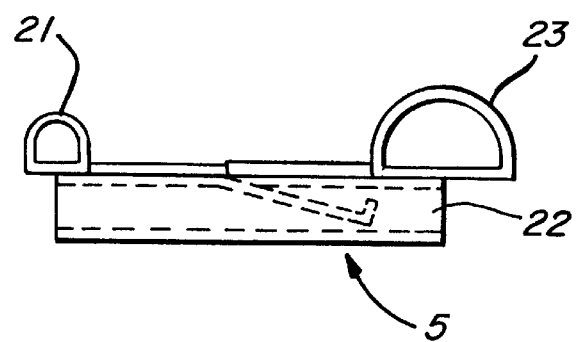
FIG. 7 is a side view of the measurement slider.

The measurement slider 5 is slidably mounted on either side 2 or 4 of the elongated support member 3 via the grooves 17 and 19. The measurement slider 5 can range from 1.25 to 2.0 inches in length, 1.25 to 1.75 inches in width and 0.15 to 0.5 inches in height. Both sides of the measurement slider 5 have an inwardly turned flange at its lower margin that rides in the respective grooves 17 and 19 of the elongated support member 3. In the preferred embodiment, the retaining clip 22, as seen in FIGS. 6 and 7, secures the measurement slider 5 in place and permits mobility by placing pressure on the elongated support member 3. It is contemplated that a coiled spring or the like may urge the upper portion of the measurement slider 5 towards the elongated support member 3 to anchor both flanges in the grooves 17 and 19 of the elongated support member 3 and thus hold the slider 5 in a position of adjustment. In order to move the slider 5 along the elongated support member 3, the operator may press in the upper portion of the slider 5 against the action of a spring with his thumb, and thus release the engagement of the flanges permitting a movement of the slider 5 longitudinally of the elongated support member 3 to a new position of adjustment.

Instead of implementing the grooves 17 and 19 for sliding and adjustment, the measurement slider 5 may capture or encompass the set of first and second sides 2, 4 and the set of first and second shorter sides 6, 8. By capturing all of the sides of the elongated support member 3, the measurement slider 5 will provide durability and resistance to typical wear and tear. A pair of ribs may be incorporated into the measurement slider 5 to fix itself in a desired position during the measurement process. The slider 5 may also be slidably mounted on either side 2 or 4 of the elongated support member 3 through guide slots.

Figure 2:
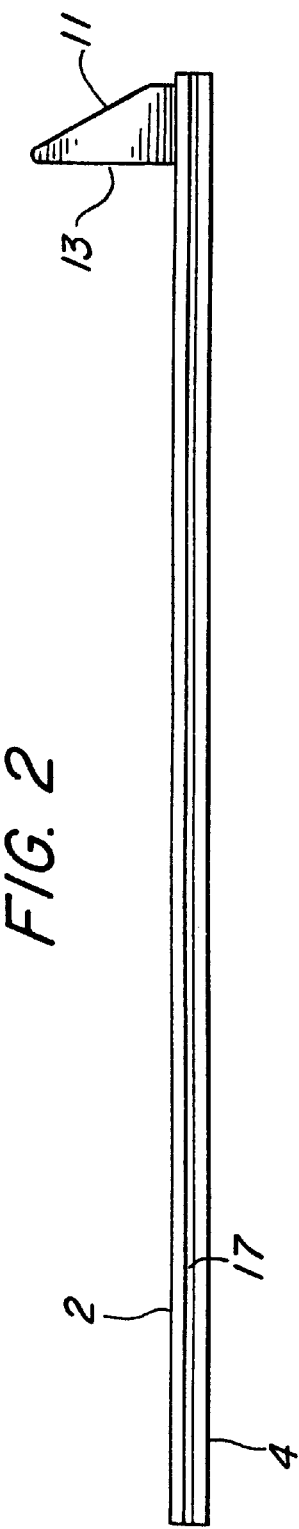
FIG. 2 is a side elevational view of a casting plate measuring device embodying principles of the instant invention.

FIG. 2 is a side elevational view of the preferred embodiment of the invention showing the positioning of the groove 17 and mounting of the fixed member 11 on the side 2 of the elongated support member 3.

Figure 3:
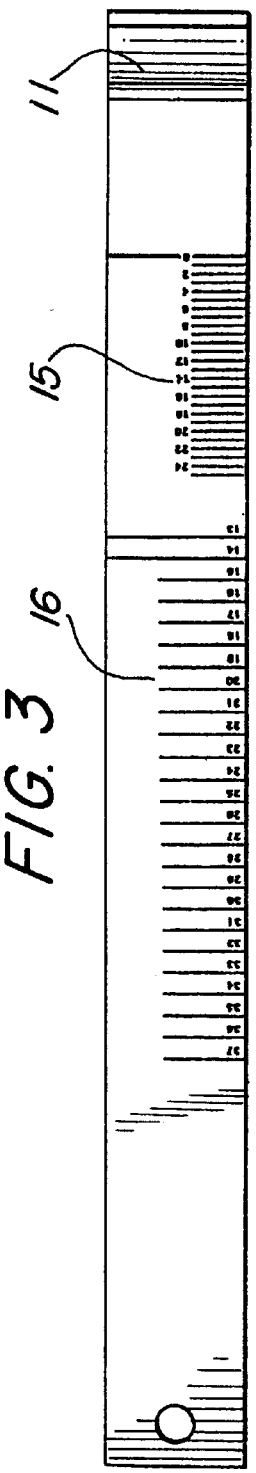
FIG. 3 is a top plan view of the structure of FIG. 2.

FIG. 3 is a top plan view of the preferred embodiment of the invention showing the positioning of scales 15 and 16 in relation to one another on the elongated support member 3 and the mounting of the fixed member 11 on the side 2 of the elongated support member 3.

Figure 4:
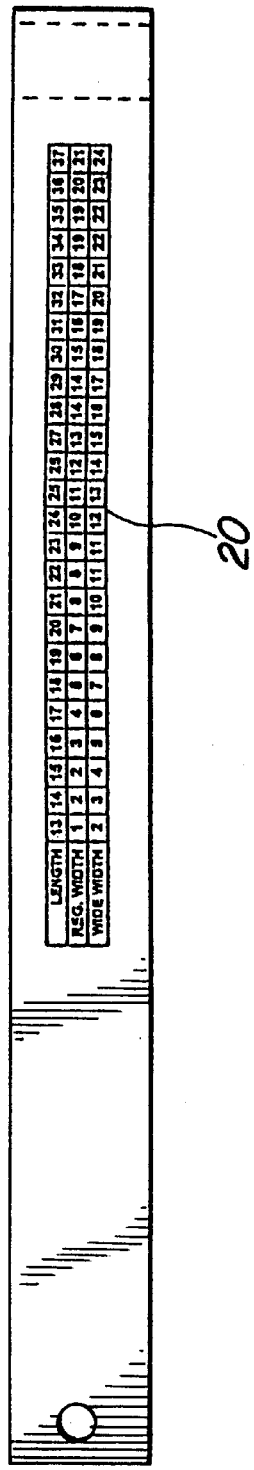
FIG. 4 is a bottom plan view of the structure of FIG. 2.

FIG. 4 is a bottom plan view of the preferred embodiment of the invention showing a reference scale 20 located on the side 4 of the elongated support member 3. The scale 20 is marked in order to indicate the size of the casting plate after the patient's length and width measurements are determined. As illustrated, the scale 20 is disposed in center of the elongated support member 3 on the side 4. It is contemplated that the scale 20 may be located adjacent either the side 6 or the side 8 of the elongated support member 3. The scale 20 may be printed, etched, silk-screened or otherwise placed on either side 2 or 4. The scale 20 may be added by any convenient means, such as, by making the marks on a carrier and placing the carrier and the markings on the elongated support member 3, as by means of decalcomania. The delcacomania process may be used in conjunction with glass, metal or plastic materials. If, for example, the elongated support member 3 was constructed of plastic, an economical method of producing a molded plastic member 3 with markings is first to mold the elongated support member 3, allow the elongated support member 3 to cool to room temperature, and then apply the markings to the surface of the elongated support member 3 to create the scale 20.

Figure 5:
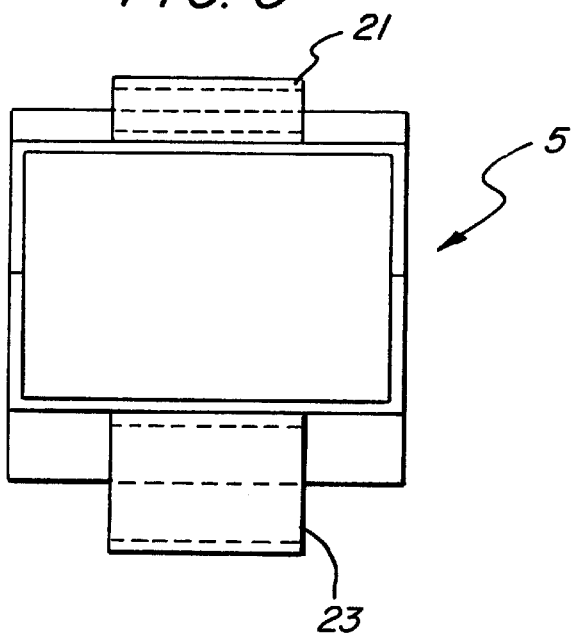
FIG. 5 is top plan view of a measurement slider or indicia member.

FIG. 5, a top plan view of the measurement slider 5, shows a small support member 21 and a large support member 23. To compensate for existing problems of no relationship on the height of the arches, the toe length is typically calculated by the calcanous to the end of the toes. However, because of the additional length created by the toe sulcus, this measurement may not be accurate. The support members 21 and 23 are designed to fit the sulci of a plurality of toes and provide a more accurate length measurement. It is contemplated that the support member 21 and/or member 23 may be shaped as an ovoid, a cube, a semi-sphere, a right circular cone, a semi-cylinder, a prism or a triangular prism. In addition, the size of support member 21 may vary from support member 23 in order to accommodate a variety of foot sizes. Members 21 and 23 may be configured in a solid shape or hollowed in order to insure flexibility or rigidity and subsequently conform to the patient's toes. Members 21 and 23 may be constructed of rubber, plastic, or any other suitable material that facilitates an accurate measurement.

FIG. 6, a front plan view of the measurement slider 5, shows a retaining clip 22. During the measurement of the patient's foot, the retaining clip 22 secures the measurement slider 5 in place and permits mobility by placing pressure on the elongated support member 3. As a result, the practitioner is able to receive an accurate measurement from a variety of patients' feet.

FIG. 7 is a side view of the measurement slider 5 in association with the retaining clip 22 and the support members 21 and 23.

Figure 8:
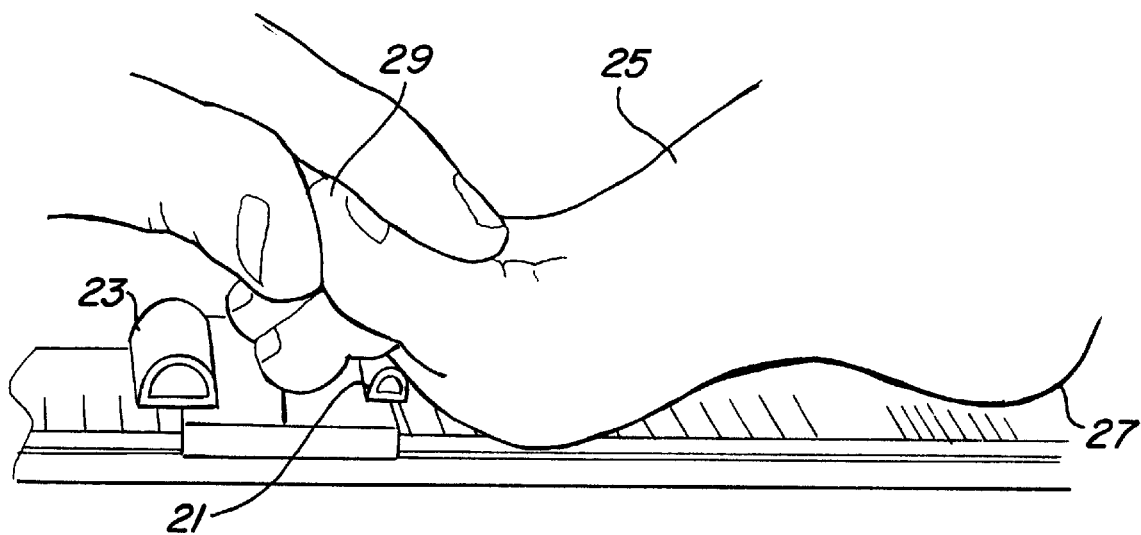
FIG. 8 is a perspective view of the casting plate measuring device showing the device as used for measuring the length of the foot.
Figure 9:
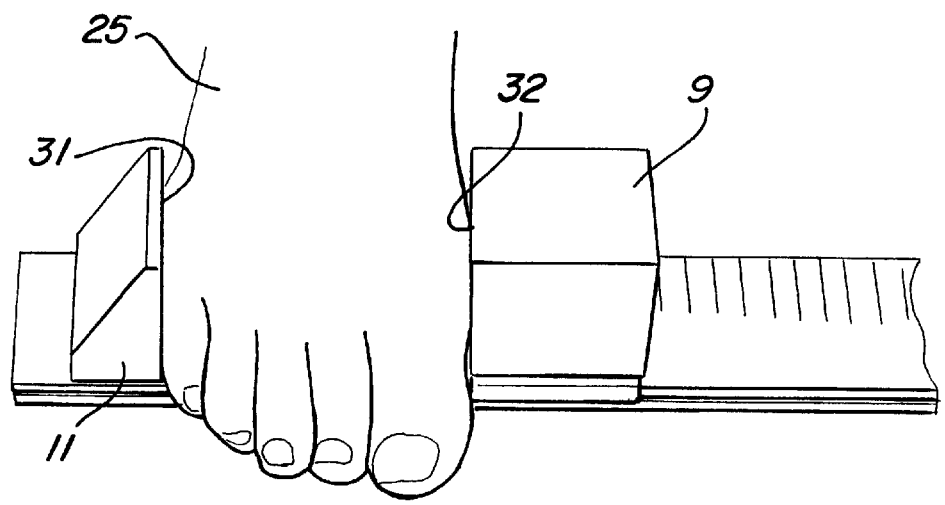
FIG. 9 is a perspective view of the casting plate measuring device showing the device as used for measuring the width of the foot.

FIG. 8 is a perspective view of the casting plate measuring device 1 showing the device 1 as used for measuring the length of a patient's foot 25. During operation of the casting plate measuring device 1 for measuring the foot 25 for an orthosis, the patient's foot 25 is placed on the elongated support member 3 with a heel 27 of the foot 25 engaging the face 13 of the fixed member 11 and the foot extending along the elongated support member 3. With the foot appropriately positioned, an orthotist, physician or practitioner positions the measurement piece 5, as seen in FIG. 9, in order to contact a toe 29 of the foot 25. In this position, the patient then may stand upon the elongated support member 3 to ensure accurate length measurement by measuring the distance between the patient's heel 27 and the midline sulcus of the toe 29 via either support member 21 or member 23, depending upon the size of the foot. The practitioner then reads the scale 16 and receives the desired length measurement.

FIG. 9 is a perspective view of the casting plate measuring device 1 showing the device 1 as used for measuring the width of the foot 25. In order to accomplish this, the patient disposes the foot 25 transversely across the elongated support member 3 with a first metatarsal head 31 contacting the fixed member 11, and the movable block member 9 is brought into position against a fifth metatarsal head 32 of the foot 25. The practitioner then reads the scale 15 and receives the desired width measurement. If the width measurement falls evenly between sizes, the practitioner will select the regular width to maximize surface definition. The proper size of the casting plate 1 for fitting a patient for an orthosis is ascertained by then inputting the width measurement into the scale 20 (FIG. 4).

Having illustrated and described the preferred embodiment and method of use as well as variants of this invention, it will be obvious to those skilled in the art that further changes and modifications may become apparent. Such changes and modifications are not to affect this instant concept and are to be considered within the scope and essence of this invention. Further, unless means plus function claim language is specifically used in the following claims, it is not the intention of the inventor to submit means plus functions claims before the United States Patent Office.

What is claimed is:

1. A casting plate size measuring device for an orthosis, comprising:
    an elongated member;
    a fixed member fastened to the elongated member;
    an indicia member slidably mounted on the elongated member with a small support member and a large support member;
    the indicia member interacts with measurement indicia indicative of the dimension of a foot; and
    the shape of the indicia member accommodates an underside of a toe.

2. The casting plate size measuring device for an orthosis of claim 1 further comprising a block slidably mounted on the elongated member.

3. The casting plate size measuring device for an orthosis of claim 1 further comprising a measurement scale on a top side of the elongated member.

4. The casting plate size measuring device for an orthosis of claim 1 further comprising a scale on a bottom side of the elongated member.

5. The casting plate size measuring device of claim 1 wherein the small and large support members are designed to fit the sulci of a plurality of toes.

6. The casting plate size measuring device of claim 1 wherein the small and large support members are in an ovoidal shape.

7. The casting plate size measuring device of claim 1 wherein the small and large support members are in a cube shape.

8. The indicia member of claim 5 wherein the small and large support members are in a semi-spherical shape.

9. The casting plate size measuring device of claim 1 wherein the small and large support members are in a right circular cone shape.

10. The casting plate size measuring device of claim 1 wherein the small and large support members are in a semi-cylindrical shape.

11. The casting plate size measuring device of claim 1 wherein the small and large support members are in a prism shape.

12. The casting plate size measuring device of claim 1 wherein the small and large support members are in a triangular shape.

13. The casting plate size measuring device of claim 1 wherein the small and large support members are solid.

14. The casting plate size measuring device of claim 1 wherein the small and large support members are hollow.

15. The casting plate size measuring device of claim 1 wherein the small and large support members are constructed of flexible material to contour to the toes.

16. The casting plate size measuring device of claim 1 wherein the small and large support members are constructed of rigid material to support the toes.

17. A casting plate size measuring device for an orthosis, comprising:
    an elongated member;
    a fixed member fastened to the elongated member;
    a block slidably mounted on the elongated member including a small support member and a large support member;
    an indicia member slidably mounted on the elongated member; and
    the indicia member is positionable relative to measurement indicia indicative of the dimension of a foot.

18. The casting plate size measuring device for an orthosis of claim 17 wherein the shape of the indicia member accommodates the underside of a toe.

19. The casting plate size measuring device for an orthosis of claim 17 further comprising a scale on a top side of the elongated member.

20. The casting plate size measuring device for an orthosis of claim 17 further comprising a scale on a bottom side of the elongated member.

21. The casting plate size measuring device of claim 17 wherein the small and large support members are designed to fit the sulci of a plurality of toes.

22. The casting plate size measuring device of claim 17 wherein the small and large support members are in an ovoidal shape.

23. The casting plate size measuring device of claim 17 wherein the small and large support members are in a cube shape.

24. The casting plate size measuring device of claim 17 wherein the small and large support members are in a semi-spherical shape.

25. The casting plate size measuring device of claim 17 wherein the small and large support members are in a right circular cone shape.

26. The casting plate size measuring device of claim 17 wherein the small and large support members are in a semi-cylindrical shape.

27. The casting plate size measuring device of claim 17 wherein the small and large support members are in a prism shape.

28. The casting plate size measuring device of claim 17 wherein the small and large support members are in a triangular shape.

29. The casting plate size measuring device of claim 17 wherein the small and large support members are solid.

30. The casting plate size measuring device of claim 17 wherein the small and large support members are hollow.

31. The casting plate size measuring device of claim 17 wherein the small and large support members are constructed of flexible material to contour the toes.

32. The casting plate size measuring device of claim 17 wherein the small and large support members are constructed of rigid material to support the toes.

33. A measuring apparatus for selecting a casting plate for a patient's foot comprising:
    a scale member with measurement indicia indicative of a heel to sulcus measurement distance; and
    a measurement unit movable along the scale member and configured to have a portion extending upward to be positioned beneath and to accommodate a sulcus of the patient's foot when a foot midline is positioned over a centerline of the scale member, the position of the measurement unit relative to the measurement indicia providing a measurement to select a casting plate for an orthosis.

34. The measuring apparatus of claim 33 further including a heel positioning member on the scale member.

* * * * *